(12) United States Patent
Schneider

(10) Patent No.: US 8,377,882 B2
(45) Date of Patent: Feb. 19, 2013

(54) STABILIZATION OF INTERLEUKIN 6 IN SERUM BASED SOLUTIONS

(75) Inventor: Christian Schneider, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/161,793

(22) Filed: Jun. 16, 2011

(65) Prior Publication Data

US 2012/0107953 A1     May 3, 2012

(30) Foreign Application Priority Data

Jul. 24, 2010 (EP) .................................. 10007718

(51) Int. Cl.
*A61K 38/20* (2006.01)
*C07K 14/54* (2006.01)

(52) U.S. Cl. ........................ 514/12.2; 530/351

(58) Field of Classification Search .................. None
See application file for complete search history.

(56) References Cited

U.S. PATENT DOCUMENTS

| 5,078,997 A | 1/1992 | Hora et al. | |
|---|---|---|---|
| 2005/0089918 A1* | 4/2005 | Horton | 435/6 |

FOREIGN PATENT DOCUMENTS

| EP | 1242576 B1 | 4/2005 |
|---|---|---|
| EP | 1882944 B1 | 3/2009 |

OTHER PUBLICATIONS

Bathrellos, Lambros M. et al., "A Highly Sensitive Enzyme-amplified Lanthanide Luminescence Immunoassay for Interleukin 6," Clinical Chemistry, 1998, pp. 1351-1353, vol. 44, No. 6.
Campbell, Patrick J., "International biological standards and reference preparations-II. Procedures used for the production of biological standards and reference preparations," Journal of Biological Standardization, 1974, pp. 259-267, vol. 2.
Christodoulides, Nicolaos et al., "A Microchip-Based Assay for Interleukin-6," Methods in Molecular Biology Microchip-Based Assay Systems Methods and Applications, Pierre N. Floriano, Editor, 2007, Chapter 10, pp. 131-144, vol. 385, Humana Press Inc., Totowa, New Jersey.
Fraunberger, Peter et al., "Validation of an Automated Enzyme Immunoassay for Interleukin-6 for Routine Clinical Use," Clinical Chemistry and Laboratory Medicine, 1998, pp. 797-801, vol. 36, No. 10.
Jensen, Wayne A. et al., "Stability Studies on Maize Leaf Phosphoenolpyruvate Carboxylase: The Effect of Salts," Biochemistry, 1995, pp. 472-480, vol. 34.
Kendrick, Brent S., "Preferential exclusion of sucrose from recombinant interleukin-1 receptor antagonist: Role in restricted conformational mobility and compaction of native state," Proceedings of the National Academy of Sciences USA, Oct. 1997, pp. 11917-11922, vol. 94.
Tarelli, E. and Wood, J. M., "Additives to biological substances. I Effect of added carbohydrates on bovine serum albumin," Journal of Biological Standardization, 1981, pp. 121-129, vol. 9.
Tarelli, Edward et al., "Recombinant Human Albumin as a Stabilizer for Biological Materials and for the Preparation of International Reference Reagents," Biologicals, 1998, pp. 331-346, vol. 26.
Timasheff, Serge N., "Control of Protein Stability and Reactions by Weakly Interacting Cosolvents: The Simplicity of the Complicated," Advances in Protein Chemistry, 1998, pp. 355-432, vol. 51, Academic Press.
Todd, Matthew J. et al., "The Structural Stability of the HIV-1 Protease," Journal of Molecular Biology, 1998, pp. 475-488, vol. 283.
Tsai, P. K. et al., "Formulation Design of Acidic Fibroblast Growth Factor," Pharmaceutical Research, 1993, pp. 649-659, vol. 10, No. 5.

* cited by examiner

*Primary Examiner* — Marianne P Allen

(57) ABSTRACT

Disclosed is a composition including IL-6, an isoform or a fragment thereof, a compound of the formula $C_{10}$-$C_{18}$-alkyl trimethylammonium halogenide (I), wherein the compound is saturated or unsaturated and/or substituted or unsubstituted, or a salt thereof, wherein the concentration of the compound in the composition is about 0.15 to about 0.4%, and a serum. Also disclosed is a kit including a composition or a lyophilisate and instructions for use. A further embodiment of the present invention is method of stabilizing IL-6, an isoform or a fragment thereof, including the steps of mixing IL-6, an isoform or a fragment thereof, a compound of the formula $C_{10}$-$C_{18}$-alkyl trimethylammonium halogenide (I), wherein the compound is saturated or unsaturated and/or substituted or unsubstituted, or a salt thereof, wherein the concentration of the compound in the composition is about 0.15 to about 0.4%, and a serum.

13 Claims, 6 Drawing Sheets

Figure 1

| | C (TTAB) % | reference | | 1 day 2-8°C | | 4 days 2-8°C | | 5 days 2-8°C | |
|---|---|---|---|---|---|---|---|---|---|
| | | C (pg/ml) | recovery (%) | C (pg/ml) | recovery (%) | C (pg/ml) | recovery (%) | C (pg/ml) | recovery (%) |
| low concentration of IL-6 | 0.05 | 34.9 | 100 | 32.4 | 93 | 30.1 | 86 | 28.6 | 82 |
| | 0.1 | 37.7 | 100 | 34.7 | 92 | 32.4 | 86 | 31.6 | 84 |
| | 0.15 | 40.9 | 100 | 39.9 | 98 | 37.0 | 91 | 36.2 | 88 |
| | 0.2 | 42.9 | 100 | 43.6 | 102 | 40.7 | 95 | 39.8 | 93 |
| | 0.25 | 40.7 | 100 | 39.0 | 96 | 39.2 | 96 | 38.4 | 94 |
| | 0.5 | 24.4 | 100 | 21.9 | 90 | 19.4 | 79 | 17.6 | 72 |
| high concentration of IL-6 | 0.05 | 192.4 | 100 | 181.5 | 94 | 168.7 | 88 | 163.7 | 85 |
| | 0.1 | 209.8 | 100 | 199.6 | 95 | 174.6 | 83 | 173.8 | 83 |
| | 0.15 | 226.3 | 100 | 220.4 | 97 | 207.8 | 92 | 202.6 | 90 |
| | 0.2 | 234.2 | 100 | 228.4 | 98 | 221.7 | 95 | 219.9 | 94 |
| | 0.25 | 247.2 | 100 | 226.8 | 92 | 229.2 | 93 | 225.7 | 91 |
| | 0.5 | 126.8 | 100 | 120.1 | 95 | 101.6 | 80 | 97.5 | 77 |

Figure 2

| | | reference | | 1 day 2-8°C | | 3 days 2-8°C | | 4 days 2-8°C | | 23 days 2-8°C | |
|---|---|---|---|---|---|---|---|---|---|---|---|
| | C (TTAB) % | C (pg/ml) | recovery (%) | C (pg/ml) | recovery (%) | C (pg/ml) | recovery (%) | C (pg/ml) | recovery (%) | C (pg/ml) | recovery (%) |
| low conc of IL-6 | no TTAB | 43.7 | 100 | 40.9 | 94 | 37.9 | 87 | 38.1 | 87 | 32.4 | 74 |
| | 0.2 | 59.3 | 100 | 57.7 | 97 | 57.0 | 96 | 57.6 | 97 | 55.4 | 93 |
| | 0.25 | 60.8 | 100 | 60.1 | 99 | 58.8 | 97 | 60.5 | 100 | 57.0 | 94 |
| high conc of IL-6 | no TTAB | 258.5 | 100 | 241.0 | 93 | 223.3 | 86 | 226.5 | 88 | 201.8 | 78 |
| | 0.2 | 347.5 | 100 | 338.2 | 97 | 336.2 | 97 | 340.5 | 98 | 329.2 | 95 |
| | 0.25 | 357.3 | 100 | 351.6 | 98 | 346.2 | 97 | 351.7 | 98 | 341.2 | 96 |

Figure 3a

| cpsn. based on human serum | | reference | | 1 day 2-8°C | | 2 days 2-8°C | | 3 days 2-8°C | | 7 days 2-8°C | | 16 days 2-8°C | | 30 days 2-8°C | |
|---|---|---|---|---|---|---|---|---|---|---|---|---|---|---|---|
| | Cpd % | pg/ml C | % rec. | pg/ml C | % rec. | pg/ml C | % rec. | pg/ml C | % rec. | pg/ml C | % rec. | pg/ml C | % rec. | pg/ml C | % rec. |
| low conc. of IL-6 | no cpd | 29.1 | 100 | 22.4 | 77 | 18.9 | 65 | 17.7 | 61 | 13.5 | 46 | 9.6 | 33 | 8.0 | 28 |
| | 0.2% TTAB | 41.0 | 100 | 34.8 | 85 | 32.5 | 79 | 29.9 | 73 | 24.6 | 60 | 19.0 | 46 | 16.6 | 40 |
| | 0.2% DTAB | 44.1 | 100 | 38.9 | 88 | 36.7 | 83 | 34.9 | 79 | 31.4 | 71 | 25.4 | 57 | 23.1 | 52 |
| | 0.2% HTAB | 39.0 | 100 | 33.3 | 85 | 30.2 | 77 | 28.7 | 74 | 24.4 | 63 | 19.7 | 50 | 17.0 | 44 |
| high conc. of IL-6 | no cpd | 169.1 | 100 | 122.1 | 72 | 105.9 | 63 | 92.1 | 54 | 72.4 | 43 | 53.8 | 32 | 45.8 | 27 |
| | 0.2% TTAB | 225.5 | 100 | 185.2 | 82 | 169.5 | 75 | 156.8 | 70 | 127.5 | 57 | 105.4 | 47 | 88.6 | 39 |
| | 0.2% DTAB | 241.8 | 100 | 208.2 | 86 | 198.3 | 82 | 184.4 | 76 | 159.2 | 66 | 134.6 | 56 | 117.1 | 48 |
| | 0.2% HTAB | 220.6 | 100 | 183.7 | 83 | 172.4 | 78 | 158.9 | 72 | 134.6 | 61 | 111.2 | 50 | 95.6 | 43 |

Figure 3b

| cpsn. based on equine serum | | reference | | 1 day 2-8°C | | 2 days 2-8°C | | 3 days 2-8°C | | 7 days 2-8°C | | 16 days 2-8°C | | 30 days 2-8°C | |
|---|---|---|---|---|---|---|---|---|---|---|---|---|---|---|---|
| | Cpd % | pg/ml C | % rec. | pg/ml C | % rec. | pg/ml C | % rec. | pg/ml C | % rec. | pg/ml C | % rec. | pg/ml C | % rec. | pg/ml C | % rec. |
| low conc. of IL-6 | no cpd | 33.6 | 100 | 31.7 | 95 | 31.1 | 93 | 29.8 | 89 | 28.7 | 85 | 26.3 | 78 | 26.5 | 79 |
| | 0.2% TTAB | 44.1 | 100 | 44.5 | 101 | 43.4 | 98 | 43.4 | 98 | 43.1 | 98 | 42.4 | 96 | 41.7 | 95 |
| | 0.2% DTAB | 44.1 | 100 | 44.7 | 101 | 44.0 | 100 | 43.7 | 99 | 42.5 | 96 | 43.1 | 98 | 42.1 | 95 |
| | 0.2% HTAB | 41.0 | 100 | 40.5 | 99 | 39.6 | 96 | 39.3 | 96 | 38.4 | 94 | 38.3 | 93 | 38.0 | 93 |
| high conc. of IL-6 | no cpd | 187.2 | 100 | 178.7 | 95 | 178.8 | 96 | 171.4 | 92 | 161.1 | 86 | 157.0 | 84 | 149.9 | 80 |
| | 0.2% TTAB | 250.9 | 100 | 250.5 | 100 | 257.3 | 103 | 248.5 | 99 | 241.5 | 96 | 244.1 | 97 | 232.6 | 93 |
| | 0.2% DTAB | 268.3 | 100 | 266.3 | 99 | 269.8 | 101 | 267.9 | 100 | 252.9 | 94 | 254.7 | 95 | 246.8 | 92 |
| | 0.2% HTAB | 247.1 | 100 | 244.5 | 99 | 245.5 | 99 | 238.4 | 96 | 230.6 | 93 | 233.2 | 94 | 220.1 | 89 |

Figure 4

| composition based on aqueous solution | | reference | | 7 day 2-8°C | | 16 days 2-8°C | | 30 days 2-8°C | |
|---|---|---|---|---|---|---|---|---|---|
| | C (compound) % | C (pg/ml) | recovery (%) | C (pg/ml) | recovery (%) | C (pg/ml) | recovery (%) | C (pg/ml) | recovery (%) |
| Low concentrations of IL-6 | no compound | 41.8 | 100 | 41.1 | 98 | 41.3 | 99 | 40.2 | 96 |
| | 0.2% TTAB | 45.5 | 100 | 33.2 | 73 | 24.7 | 54 | 21.2 | 47 |
| | 0.2% DTAB | 53.1 | 100 | 43.1 | 81 | 36.2 | 68 | 32.0 | 60 |
| | 0.2% HTAB | 41.4 | 100 | 25.0 | 60 | 17.6 | 42 | 13.9 | 34 |
| High concentrations of IL-6 | no compound | 239.6 | 100 | 231.0 | 96 | 235.7 | 98 | 231.3 | 97 |
| | 0.2% TTAB | 252.3 | 100 | 178.2 | 71 | 135.6 | 54 | 108.2 | 43 |
| | 0.2% DTAB | 285.0 | 100 | 229.5 | 81 | 193.5 | 68 | 164.6 | 58 |
| | 0.2% HTAB | 237.7 | 100 | 140.8 | 59 | 96.5 | 41 | 73.9 | 31 |

Figure 5

|  | reference | | 7 days 2-8°C c(pg/mL) | | 7 days 2-8°C recovery(%) | |
| --- | --- | --- | --- | --- | --- | --- |
|  | no TTAB | 0.225% TTAB | no TTAB | 0.225% TTAB | no TTAB | 0.225% TTAB |
| equine serum | 234.7 | 279.0 | 187.4 | 254.2 | 80 | 91 |
| bovine serum | 254.2 | 272.4 | 175.4 | 167.0 | 69 | 61 |
| mouse serum | 246.2 | 272.4 | 180.7 | 231.3 | 73 | 85 |

STABILIZATION OF INTERLEUKIN 6 IN SERUM BASED SOLUTIONS

RELATED APPLICATIONS

This application claims priority to European application EP 10007718.9 filed Jul. 24, 2010.

FIELD

The present invention relates to a composition comprising interleukin 6 (IL-6), an isoform or a fragment thereof, a compound of the formula $C_{10}$-$C_{18}$-alkyl trimethylammonium halogenide (I), wherein the compound is saturated or unsaturated and/or substituted or unsubstituted, or a salt thereof, wherein the concentration of the compound in the composition is about 0.15% to about 0.4%, and a serum. Also provides is a compound for stabilization of interleukin 6 for the quantitative determination in immunoassays, receptor based assays or other assays.

BACKGROUND

Interleukin-6 (IL-6) is a pleiotropic cytokine with a wide range of functions. It was first described as interferon-β2 plasmacytoma growth factor, and hepatocyte stimulating factor. Later on it was described as human B-cell-stimulating factor (BSF2). In 1988 it was proposed to name it IL-6 as further studies have demonstrated that the protein also shows activities not only on B-cells but also on T-cells, hematopoietic stem cells, hepatocytes and brain cells.

IL-6 is produced from a single gene encoding a product of 212 amino acid peptide with a molecular weight between 22-27 kDA. Further, it was reported that also immunoreactive complexes in the range of 60-70 kDA were detected in human body fluids in patients with acute bacterial infections.

IL-6 belongs to the cytokine-family. Cytokines are small molecules secreted from one cell that signals to other cells by binding to its specific receptor. An interleukin is generally a cytokine produced by leucocytes. Pro-inflammatory cytokines (IL-1, IL-6) are predominantly produced by activated immune cells involved in the amplification of inflammatory reactions. Anti-inflammatory cytokines (IL-1 receptor antagonist, IL-4, IL-6, IL-10, IL-11, IL-13) act in concert with specific cytokine inhibitors and soluble cytokine receptors to control the pro-inflammatory cytokine response. IL-6 plays a crucial role as well by being the chief stimulator of acute-phase proteins, e.g., CRP, as well as by controlling the level of proinflammatory response. In homeostasic conditions IL-6 concentrations are low whereas under stress conditions amounts of IL-6 increase quickly.

IL-6 production is rapidly induced in the course of acute inflammatory reactions associated with injury, trauma, stress, infection, brain, death, neoplasia, and other situations.

The quantitative determination of IL-6 in serum and plasma may be performed by using immunoassays. The lack of stability of IL-6 protein in the liquid phase is a major disadvantage of the current IL-6 detection assays, and the available methods for the stabilization of proteins are not suitable to stabilize IL-6 (Chamani, A. A. et al., J. Colloid Interface Sci. 297 (2006) 561).

Protein stabilization methods can be divided into two classes. First, stabilization is performed to prevent or minimize chemical modifications of the protein, e.g., protection against oxidation reactions. Chemical modifications are based on changes regarding covalent atom-bonds. More precisely, chemical modifications encompass deamidation reactions, oxidations, hydrolysis and cleavage or formation of new disulfidbridges. Stabilization against chemical modifications of a given protein is often achieved by changes in pH and buffer composition. Formation of new disulfidbridges can be prevented by use of specific protection groups for thiols. Functional groups sensitive towards oxidation can be protected by use of scavenger reagents. Protection is achieved by preferential oxidation of the scavenger.

Secondly, a given protein can be stabilized to prevent physical modifications of the protein, e.g., protection of the protein against conformational changes in the protein structure. Different strategies may be used to prevent these conformational changes. Timasheff S. N., Control of protein stability and reactions by weakly interacting cosolvents. Adv. Protein Chem. 91 (1998) 355-432, describe the addition of certain excipients such as sugars, salts, polyalcohols to stabilize protein in solution. When present in high concentration, these excipients protect against deterioration of the activity and maintain proteins in a functional state.

However, Kendrick B. S., Preferential exclusion of sucrose from recombinant interleukin-1 receptor antagonist: Role in restricted conformational mobility and compaction of native state. PNAS USA 94 (1997) 11917-11922, disclose that, in the presence of sucrose, increases in protein surface area of the interleukin 1 receptor antagonist are more thermodynamically unfavorable than in water. The equilibrium between states is shifted towards that with the smallest surface area. Jensen W. A., Stability studies on maize leaf phosphoenoloyruvate carboxylase: The effect of salts. Biochemistry 34 (1995) 472-480, describes the effect of high concentrations of several salts on the stability of PEPC in solution. Tsai P. K. Use of specific ligands, e.g. use of Heparin for stabilization of aFGF Formulation design of acidic fibroplast growth factor. Pharm Res 10 (1993) 649-659 found that a wide variety of polyanions stabilize acidic fibroblast growth factor (aFGF) by raising the temperature at which the protein unfolds. Campell P J. Et al., II. Procedures used for the production of biological standards and reference preparations. J Biol Stand 2 (1974) 259-267, describe methods for achieving stable and reliable biological standards and reference preparations. The effect of added carbohydrates on the chemical composition and antigenic activity of, e.g., bovine serum albumin is reported in Tarelli E, et al., Additives to biological substances. I. Effect of added carbohydrates on bovine serum albumin. J Biol Stand; 9 (1981) 121±130. Furthermore, Tarelli E, et al., Recombinant human albumin as a stabilizer for biological materials and for the preparation of international reference reagents. Biologicals [1045-1056] (1998) vol: 26 iss: 4 pg: 331, show that recombinant human albumin can be used as a stabilizer for biological materials and for the preparation of international reference reagents. Todd M. J. et al., Dimerization of sensitive proteins the structural stability of the HIV-1 protease. J Mol boil 283 (1998) 475-488, describes that dimerization of sensitive proteins, e.g., HIV-1 protease leads to the structural stability of the protein. Finally, Lougheed W. D. et al., Use of neutral surfactants: Physical stability of insulin formulations. Diabetes (1983) 34:424, describes that the aggregation of insulin into high-molecular-weight polymers may be inhibited by reducing the effective polarity of the solvent.

However, the hitherto known method for stabilizing proteins suffer from the disadvantage that they do not allow sufficient stabilization of IL-6 and in particular of IL-6 in serum.

Consequences of the reduced IL-6 stability are difficulties during the production of IL-6 based reagents, such as restrictions in maximum process times, reduced lot sizes due to the available short process time and limited half life of IL-6. To compensate for IL-6 loss during process time, additional IL-6 has to be added during the inprocess-control which results in increased cost. On the customer side, the reduced stability leads to inconveniently short stability of IL-6 products, e.g., calibrators or quality control materials.

EP 1882944 describes tetradecyl trimethylammonium bromide (TTAB) as a denaturing agent for demasking the epitopes responsible for antibody binding on amyloid-peptide oligomers by removing attached proteins.

US 2004/0157218 discloses a method of treating a biological sample for extraction of nucleic acid, dodecyl trimethylammonium bromide (DTAB) and cethyl trimethylammonium bromide (CTAB) are utilized as the detergent for denaturation of the protein. WO 2009/048962 discloses a separation medium for capillary electrophoretic size separation of proteins in the presence of a compound.

EP 1566437 discloses a method for adsorbing a nucleic acid from a biological sample to a solid phase. CTAB is disclosed as a detergent in the lysis buffer for protein denaturation. Thus, according to the above documents CTAB and DTAB are used to destabilize proteins rather than stabilizing them.

EP 1242576 discloses an aqueous reagent composition to enhance the stability of antigens. The disclosed reagent composition comprises a buffer, a protein-rich blocking agent comprising a mixture of protein and/or polypeptides and having a total protein concentration of from 1 to 50 g %, a solubilizing agent, a salt, a chelating agent, a detergent, and a preservative and having a final pH of 7.5 to 8.5. The preservative may be compound trimethyltetradecylammonium bromide (TTAB) in a final concentration of 0.01% w/v, preferably between 1% and 0.1%. Furthermore, the protein rich blocking agent may be fetal calf serum in a concentration of (5%) w/v. Notably, the preservative TTAB is used to prevent growth of microorganism and not to stabilize antigens.

There is experimental evidence showing that most part of the concentration range for TTAB and the low serum concentration disclosed in EP 1242576 does not stabilize IL-6. On the contrary, under these conditions TTAB even leads to an increased destabilization of IL-6.

A need for a method and means to increase the stabilization of IL-6 still remains. It is therefore the aim of the present invention to find conditions which lead to an improved stability of IL-6 used for quality control material, calibrators, receptor based assays or other assays.

SUMMARY

The invention solves the problem of insufficient IL-6 stability in serum by use of a composition as a stabilizing agent according to the claims of the invention.

Surprisingly, using several concentration ranges it became evident that only a narrow window of concentration of these compounds improves the stability of IL-6 in serum. The invention provides for better increased recovery of IL-6 compared to solutions without these compounds.

In one aspect, the invention is directed to a composition comprising IL-6, an isoform or a fragment thereof, a compound of the formula $C_{10}$-$C_{18}$-alkyl trimethylammonium halogenide (I), wherein the compound is saturated or unsaturated and/or substituted or unsubstituted, or a salt thereof, wherein the concentration of the compound in the composition is about 0.15 to about 0.4%, and a serum.

In a further aspect, the invention is directed to a lyophilisate suitable for reconstitution into a composition according to the embodiments described herein, comprising IL-6, an isoform or a fragment thereof, a compound of the formula $C_{10}$-$C_{18}$-alkyl trimethylammonium halogenide (I), wherein the compound is saturated or unsaturated and/or substituted or unsubstituted, or a salt thereof, and a serum.

In another aspect, the present invention is directed to a kit comprising a composition or a lyophilisate and an instruction for use.

In a further aspect, the invention is directed to a method of producing a composition comprising the steps of mixing IL-6, an isoform or a fragment thereof, a compound of the formula $C_{10}$-$C_{18}$-alkyl trimethylammonium halogenide (I), wherein the compound is saturated or unsaturated and/or substituted or unsubstituted, or a salt thereof, wherein the concentration of the compound in the composition is about 0.15% to about 0.4%, and a serum, optionally lyophilizing the mixture of step A.

A further aspect of the present invention is a method of stabilizing IL-6, an isoform or a fragment thereof, comprising the steps of mixing IL-6, an isoform or a fragment thereof, a compound of the formula $C_{10}$-$C_{18}$-alkyl trimethylammonium halogenide (I), wherein the compound is saturated or unsaturated and/or substituted or unsubstituted, or a salt thereof, wherein the concentration of the compound in the composition is about 0.15 to about 0.4%, and a serum.

In another aspect, the present invention is directed to the use of a compound of the formula $C_{10}$-$C_{18}$-alkyl trimethylammonium halogenide (I), wherein the compound is saturated or unsaturated and/or substituted or unsubstituted, or a salt thereof, for stabilizing IL-6, an isoform or a fragment thereof.

BRIEF DESCRIPTION OF THE DRAWINGS

FIG. 1 shows results of the IL-6 recovery depending on the TTAB concentration. TTAB was varied from 0.05 to 0.5%. Surprisingly a stabilization effect is observed for TTAB concentration of 0.05% to below 0.5%, in particular for 0.15%-0.25%. In contrast, a concentration of 0.5% TTAB leads to destabilization of IL-6. Samples were stored up to five days at 2-8° C. Samples were stored up to five days at 2-8° C.

FIG. 2 shows results of the IL-6 recovery at three concentrations of TTAB (0 as negative control, 0.2% and 0.25%). Samples were stored up to 23 days at 2-8° C. Results shown in FIG. 1 were confirmed. Compared to the negative control a 20% and 17% increase in the IL-6 recovery in L1 and L2 was achieved (L1 describes a low level of IL-6, in the range of 43.7 to 60.8 pg/mL, while L2 describes a high level of IL-6, in the range of 258.5 to 357.3 pg/mL).

FIGS. 3a and 3b show results of the IL-6 recovery in the presence of TTAB, DTAB or HTAB in a composition based on human (3a) and a composition based on equine serum (3b) in comparison to the recovery in human or equine serum without the addition of TTAB, DTAB or HTAB. Samples were stored up to 30 days at 2-8° C.

FIG. 4 shows results of the IL-6 recovery in the presence of TTAB, DTAB or HTAB in an aqueous buffer containing 3% serum protein, in comparison to the recovery in the same buffer without addition of TTAB, DTAB and HTAB. Samples were stored up to 30 days at 2-8° C. Results clearly indicate the detrimental effect of TTAB, DTAB and HTAB on the stability of the IL-6 in aqueous buffer containing 3% serum protein, in contrast to results observed in serum (FIGS. 1-3).

FIG. 5 shows results of the IL-6 recovery in the presence of 0.225% TTAB in pH 7 HEPES buffered sera (equine serum, bovine serum, sheep serum and mouse serum). Samples were stored 7 days at 2-8° C. These results indicate the stabilization of IL-6 in equine serum, sheep serum and mouse serum, but not in bovine serum. In bovine serum TTAB leads to a decreased stability of IL-6.

DETAILED DESCRIPTION

In a first preferred aspect, the present invention relates to a composition comprising IL-6, an isoform or a fragment thereof, a compound of the formula $C_{10}$-$C_{18}$-alkyl trimethylammonium halogenide (I), wherein the compound is saturated or unsaturated and/or substituted or unsubstituted, or a salt thereof, wherein the concentration of the compound in the composition is about 0.15% to about 0.4%, and a serum.

In the context of the present invention, "interleukin-6 (IL-6)" is preferably meant to encompass IL-6, as it is known in the art. Preferably, IL-6 encompasses interferon-I 2, plasmacytoma growth factor, hepatocyte stimulating factor and human B-cell-stimulating factor 2 (BSF2). IL-6 is preferably a protein produced from a single gene encoding a product of 212 amino acids, more preferably the 184 amino acid IL-6 peptide which is cleaved at the N-terminus of the 212 amino acid peptide (Song M, Kellum J A. Interleukin-6. Crit. Care Med 2005; 33 (Suppl 12): 463-465). Preferably, IL-6 encompasses free IL-6 which is not bonded to its receptor IL-6R. Moreover, IL-6 may also encompass IL-6 in the state of the IL-6/IL-6R complex (Taga T et al., Drucker C, Gewiese J, Malchow S, Scheller J, Rose-John S. Impact of Interleukin-6 Classic- and Trans-signaling on Liver Damage and Regeneration. J Autoimm 2009, in press). Preferably, IL-6 is the IL-6 protein which can be bound or which is bound by the monoclonal anti-IL6 antibody M-BE8 (as defined in EP0430193, i.e., an antibody produced by the cell line BE-8, or in Klein, B., et al. 1991, Murine anti-interleukin 6 monoclonal antibody therapy for a patient with plasma cell leukemia, Blood 78, 1198-1204) or M-23C7. Preferably, IL-6 is the IL-6 which can be bound or which is bound by the antibody of Roche's IL-6 assay for use on ELECSYS and cobas immunoassay systems (Roche). The term IL-6 also preferably encompasses a variant of the aforementioned IL-6, preferably of human IL-6. The variant encompasses a protein or peptide substantially similar to the specific reference IL-6 molecule, preferably to the human IL-6. The term substantially similar is well understood by the person skilled in the art. In particular, a IL-6 variant may be an isoform or allele which shows at least one amino acid exchange (and preferably up to about 25, more preferably up to about 15, more preferably up to about 10, more preferably up to about 5, most preferably up to about 3 amino acid exchanges) compared to the amino acid sequence of the specific reference IL-6 molecule. Preferably, such a IL-6 variant has a sequence identity to the specific reference IL-6 molecule of at least about 80%, preferably at least about 85%, more preferably at least about 90%, most preferably at least about 95%, most preferably at least about 98%, preferably with respect to human IL-6, even more preferably over the entire length of the human IL-6. The degree of identity between two amino acid sequences can be determined by algorithms well known in the art.

Preferably, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the homology alignment algorithm of Needleman and Wunsch, by the search for similarity method of Pearson and Lipman, Proc. Natl. Acad Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG) or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Variants referred to above may be allelic variants or any other species specific homologs, paralogs, or orthologs. The expression variant also encompasses also degradation products, e.g., proteolytic degradation products, which are still recognized by the diagnostic means or by ligands directed against the respective full-length protein or peptide. The term "variants" is also meant to cover splice variants. The term "variant" also relates to a post-translationally modified peptide such as glycosylated peptide. A "variant" is also a peptide which has been modified after collection of the sample, for example by covalent or non-covalent attachment of a label, particularly a radioactive or fluorescent label, to the peptide. Preferably, the IL-6 variant possesses essentially the same immunological and/or biological properties of the specific reference peptide, preferably the same immunological and/or biological properties as human IL-6, most preferably the same biological and/or immunological properties as human IL-6. Preferably the IL-6 variant displays at least about 70%, preferably at least about 80%, preferably at least about 90%, preferably at least about 95%, preferably at least about 98% of the human IL-6 activity. The IL-6 activity, is preferably the IL-6 receptor binding activity (Taga T, Kishimoto T. Gp130 and the Interleukin-6 Family of Cytokines. Annu. Rev. Immunol. 1997; 15: 797-819; Drucker C, Gewiese J, Malchow S, Scheller J, Rose-John S. Impact of Interleukin-6 Classic- and Trans-signaling on Liver Damage and Regeneration. J Autoimm 2009, in press). Preferably the IL-6 variant displays a human IL-6 receptor binding activity of at least about 80%, preferably at least about 90%, preferably at least about 95% of human IL-6.

A compound of the present invention is a compound of the formula $C_{10}$-$C_{18}$-alkyl trimethylammonium halogenide (I), more preferably to the formula $C_{12}$-$C_{16}$-alkyl trimethylammonium halogenide (II). The halogenide of the compound is preferably selected from fluoride, chloride, bromide, or iodide, more preferably bromide.

Preferably, the compounds as used herein are selected from C10, C11, C12, C13, C14, C15, C16, C17 or C18 alkyl trimethylammonium halogenide, more preferably from C12, C13, C14, C15 or C16 alkyl trimethylammonium halogenide. The CAS-numbers of case compounds are 1119-97-7, 1119-94-4, 1112-00-5, 57-09-0, 19727-46-9, 4574-04-3, 73163-54-9, 112-02-7, 1885-15-0, 112-03-8, 77544-88-8, 879685-36-6, 1120-02-1, 21424-24-8, 57-09-0, 21424-22-6, 1119-97-7, 21424-21-5, 1119-94-4, 2650-58-0, 67867-02-1, 19014-04-1, 205582-59-8, 15934-10-8, 7192-88-3, 82539-37-5.

Preferably, said compounds are tetradecyl trimethylammonium bromide (TTAB), or dodecyl trimethylammonium bromide (DTAB) or hexadecyl trimethylammonium bromide (HTAB). TTAB relates to the compound tetradecyltrimethylammonium bromide, CAS-number 1119-97-7. DTAB relates to the compound dodecyl trimethylammonium bromide, CAS-number 1119-94-4. HTAB relates to the compound hexadecyl trimethylammonium bromide, CAS-number 57-09-0.

The compound of the present invention is saturated or unsaturated. Preferably, the compound is an alkane, alkene or alkine.

Furthermore, the compound of the present invention is substituted or unsubstituted. The term "substituted compound" as used herein, describes a compound where at least one hydrogen atom is replaced by an residue R. R is H, hydroxyl, thiol, a halogenid selected from fluorid, chloride bromide or iodite, a C1-C4 compound selected one of the following: linear, branched or cyclic alkyl, optionally substituted, and linear branched or cyclic alkenyl, wherein the optional substitutents are selected from one or more alkenylalkyl, alkynylalkyl, cycloalkyl, cycloalkenylalkyl, arylalkyl, heteroarylalkyl, heterocyclealkyl, optionally substituted heterocycloalkenylalkyl, arylcycloalkyl, and arylheterocycloalkyl, each of which is optionally substituted wherein the optional substitutents are selected from one or more of alkenylalkyl, alkynylalkyl, cycloalkyl, cyclalkenylalkyl, arylalkyl, alkylaryl, heteroarylalkyl, heterocyclealkyl, optionally substituted heterocycloalkenylalkyl, arylcycloalkyl, and arylheterocyclalkyl, phenyl, cyano, hydroxyl, alkyl, aryl, cycloalkyl, cyano, alkoxy, alkylthio, amino, —NH (alkyl), —NH(cycloalkyl)2, carboxy and —C(O))-alkyl.

The term "stabilization" as used herein refers to the conservation of the structural integrity or at least to the biological activity of IL-6. Preferably, "stabilized IL-6" refers to an IL-6 which prolongs the shelf life of IL-6. Preferably, "stabilized IL-6" is an IL-6 which when tested under conditions defined in the examples displays a % of recovery upon storage of an IL-6 composition of the invention for 7 days at 2-8° C. of at least about 60%, preferably at least about 80%.

Interestingly, applicant have found that a concentration of about 0.15% to about 0.4% of the compound of the present invention in the IL-6 containing (liquid) composition leads to a stabilization of IL-6. More preferably, the concentration of said compound is about 0.15% to about 0.25%. Furthermore, a concentration of greater than about 0.5% of said compound and a concentration of less than 0.05% of said compound leads to destabilization of IL-6 (interleukin-6) in serum.

In particular, the present invention shows that the IL-6 recovery depends on the TTAB concentration, which was varied from about 0.05% to about 0.5%. The strongest stabilizing effect is observed for a concentration of TTAB from about 0.2% and about 0.25%. A concentration of about 0.5% TTAB leads to destabilization of IL-6. The IL-6 recovery could also be confirmed by using different concentrations of TTAB (0% as negative control, 0.2% and 0.25%). Compared to the negative control, a 20% and a 17% increase in the IL-6 recovery in low and high concentration of IL-6 was achieved after 23 days at 2-8° C.

The provision of IL-6 with elevated stability improves the production of immunological reagents, alleviates restrictions in maximum process times and increases the IL-6 lot sizes. Preferably, no further addition of IL-6 during the inprocess-control is necessary to compensate for loss of unstabilized IL-6.

Thus, a decreased cost of IL-6 based products is caused by a higher stability of IL-6. On the customer side the increased stability of IL-6 leads to longer stability claims of respective products, e.g., calibrators or quality control materials.

The IL-6 stabilizing effect is not limited but extends the other compounds of the invention. It could, e.g., be shown (FIGS. 3a and 3b) that the compounds TTAB, DTAB and HTAB at the indicated concentration in human and in equine serum strongly stabilize IL-6 in comparison to the recovery in human or horse serum without the addition of TTAB, DTAB or HTAB. The samples were stored up to 30 days at 2-8° C.

The IL-6 recovery is further evident in the presence of TTAB, DTAB and HTAB in an aqueous buffer containing 3% protein in comparison to the recovery in the same buffer without addition of TTAB, DTAB and HTAB. Samples were stored up to 30 days at 2-8° C. These results clearly indicate the detrimental effect of TTAB, DTAB and HTAB on the stability of the IL-6 in aqueous solution, in contrast to results observed in serum.

The IL-6 recovery in the presence of 0.225% TTAB in HEPES buffered serum (FIG. 5) indicates that the positive effect of TTAB on the stability of IL-6 is not only performed in equine serum but also in sheep and mouse serum. No positive effect of TTAB was performed on bovine serum, which could be traced back to a different composition of hormones and/or vitamin B12 in the equine serum compared to the serum from other species.

The IL-6 stabilizing effect of the compound of the invention is not limited to a particular serum type. A further aspect of the present invention is that the serum as used herein is a mammalian serum, preferably selected from human, equine, bovine, sheep or mouse serum. Preferably, the serum is a mammalian serum which is not sheep serum, or not sheep or bovine serum. The term "serum" as used herein refers to a solution based on serum containing a buffer. The addition of substances like salts, buffers, sugars, a chelating agents, preservatives and protease inhibitors to the serum of the present invention is preferred but not necessary. The term "equine serum" as used herein refers to serum obtained from horses. The term "bovine serum" as used herein refers to serum obtained from bovine. The term "sheep serum" as used herein refers to serum obtained from sheep. The term "mouse serum" as used herein refers to serum obtained from mouse.

Preferably, the serum concentration in the composition of the invention is at least about 60%, more preferably about 70%, more preferably about 80%, much more preferably about 90%, and most preferably about 95%.

A sugar may be added to the composition of the invention. The term "sugar" as used herein refers to any monosaccharide or disaccharide. Preferably "sugar" refers to D-Glucose and/or D-Mannose. The sugar is preferably a polyol, more preferably mannit. The term "polyol" as used herein refers to any sugar alcohol. Preferably "polyol" refers to D-Mannitol and/or racemic Mannitol, CAS number 69-65-8.

A chelating agent may be added to the composition of the invention. The term "chelating agent" as used herein refers to a bi- or multidentate ligand. Preferably "chelating agent" refers to EDTA (ethylenediaminetetraacetic acid) and/or EDDS (ethylenediamine-N,N'-disuccinic acid).

A preservative may be added to the composition of the invention. The term "preservative" as used herein refers to compounds used for preserving diagnostic reagents as described in EP0467337. Preferably, the term "preservative" relates to the compound 2-Hydroxy-pyridin-N-oxid, available under the brand name Oxy-Pyrion (2-Hydroxypyridin-N-oxid) from Pyrion-Chemie.

A protease inhibitor may be added to the composition of the invention. The term "protease inhibitor" as used herein refers to a compound and/or mixture of compounds preventing proteolytic decay caused by Chymotryspsin, Thermolysin, Papain, Pronase, Pancreatic extracts and Trypsin. Preferably "protease inhibitor" relates to a product available from Roche (Protease Inhibitor Cocktail complete, Cat. No. 11697498001).

Preferably, a buffer is added to composition of the invention or to the serum. The buffer preferably comprises at least one of the following compounds: Phosphate (Sodium or Potassium phosphate), N-2-hydroxyethylpiperazin-N-2-ethanesulfonic acid (HEPES), 3-N-morpholino-2-hydroxypropanesulfonic acid (MOPSO), 3-morpholinopropanesulfonic acid (MOPS), N,N-bis-2-hydroxyethyl-2-aminoethanesulfonic acid (BES), tris-hydroxymethylaminoethane (TRIS) or triethanolamine (TEA). Preferably, the buffer of the present invention is HEPES.

In the serum of the present invention IL-6 is added to 50 mM HEPES buffered based on equine, bovine, sheep, human or mouse serum. The final pH of the composition is between 6.5 to 7.5, most preferable the final pH of the composition is 7.0.

Another aspect of the present invention relates to a lyophilisate suitable for reconstitution into a composition according to the present invention, comprising IL-6, an isoform or a fragment thereof, a compound of the formula $C_{10}$-$C_{18}$-alkyl trimethylammonium halogenide (I), wherein the compound is saturated or unsaturated and/or substituted or unsubstituted, or a salt thereof, and a serum.

The term "lyophilisate" as used herein refers to a composition of the invention obtained by a freeze-drying process. The concentration of the ingredients in the lyophilisate is set such the lyophilisate upon reconstitution with a defined volume of a defined liquid composition (e.g., distilled water) results in a composition of the invention.

Another aspect of the present invention relates to a kit comprising a composition or a lyophilisate according to the present invention and an instruction for use.

In another aspect it is provided a method of producing a composition of the present invention or a lyophilisate of the present invention,
comprising the steps of
A) mixing
  i) IL-6, an isoform or a fragment thereof,
  ii) a compound of the formula $C_{10}$-$C_{18}$-alkyl trimethylammonium halogenide (I),
    wherein the compound is saturated or unsaturated and/or substituted or unsubstituted, or a salt thereof, wherein the concentration of the compound in the composition is about 0.15%-about 0.4%, and
  iii) a serum,
optionally lyophilizing the mixture obtained in step A.

In another aspect it is provided a method of stabilizing IL-6, an isoform or a fragment thereof comprising the steps of mixing
  i) IL-6, an isoform or a fragment thereof,
  ii) a compound of the formula $C_{10}$-$C_{18}$-alkyl trimethylammonium halogenide (I), wherein the compound is saturated or unsaturated and/or substituted or unsubstituted, or a salt thereof,
    wherein the concentration of the compound in the composition is about 0.15% to about 0.4%, and
  iii) a serum.

Another aspect of the present invention relates to the use of a compound of the formula $C_{10}$-$C_{18}$-alkyl trimethylammonium halogenide (I), wherein the compound is saturated or unsaturated and/or substituted or unsubstituted, or a salt thereof, for stabilizing
IL-6, an isoform or a fragment thereof. Preferably, the compound in the IL-6 composition has a concentration of about 0.15% to about 0.4%, preferably about 0.15%-0.25%.

Preferably, the composition further comprises a serum, preferably a buffered serum. Preferably, the compound is of the formula $C_{12}$-$C_{16}$-alkyl trimethylammonium halogenide (II), wherein the halogenide is selected from fluoride, chloride, bromide, or iodide. Preferably, the compound is selected from tetradecyl trimethylammonium bromide, dodecyl trimethylammonium bromide or hexadecyl trimethylammonium bromide.

Stabilized IL-6 of the present invention can be used as a single or multi analyte control and/or single or multi analyte calibrator.

The term "control" as used herein refers to a quality control material which is essential for the measurement of an analyte, e.g., IL-6. The term "single-analyte control" as used herein refers to a quality control material containing one analyte. The term "multi-analyte control" as used herein refers to a quality control material containing more than one analyte.

Most instruments and sensors are designed to meet certain accuracy specifications; the process of adjusting an instrument to meet those specifications is referred to as calibration. The device used to calibrate other instruments is known as a calibrator. Calibrators vary in form and function depending on the instruments with which they are designed to work. The term "multi-analyte calibrator" as used herein refers to a calibrator containing more than one analyte.

The term "about" as used herein encompasses a range of + and −20% to the specific value, amount, concentration, level, etc. indication of a value of "about 100%" is meant to encompass a value of a numerical range of 100+/−20%, i.e., a value range from 80 to 120. Preferable the term "about" encompasses a range of + and −10% relative to the specific value, amount, concentration, level etc, most preferably a range of + and −5% relative to the specific value, amount, concentration, level, etc.

EXAMPLES

Shown are results from four experiments in total. First two datasets indicate the stabilization of IL-6 in a composition based on equine serum. IL-6 is always tested in two concentrations described as low (24-60 pg/mL) and high (126-357 pg/mL). The third dataset indicates stabilization in equine serum and in human serum. The fourth dataset shows the negative effect of compounds on the stability of IL-6 in an aqueous based composition containing 3% serum protein.

The composition contains serum with HEPES (50 mM). IL-6 was measured using the ELECSYS IL-6 Immunoassay from Roche (Id. 05109442190). TTAB relates to the compound Tetradecyltrimethylammonium bromide, CAS-number 1119-97-7. DTAB relates to the compound Dodecyl trimethylammonium bromide, CAS-number 1119-94-4. HTAB relates to the compound Hexadecyl trimethylammonium bromide, CAS-number 57-09-0.

All measurements were performed on the ELECSYS 2010 analyzer from Roche Diagnostics. The Roche Diagnostics ELECSYS 2010 Immunoassay System is a fully automated, software-controlled system for immunoassay analysis. It is designed for both quantitative and qualitative in vitro determinations using a large variety of tests for analysis. The detection system is based on the electro-chemiluminescence technology using an electrode and analyte specific, labeled antibodies. The reagent used in all measurements is the ELECSYS IL-6 assay from Roche, cat. no. 05109442190. This assay uses the so called sandwich principle, details given below:
  1st incubation: 30 μL of sample are incubated with a biotinylated monoclonal IL-6-specific antibody.

2nd incubation: After addition of a monoclonal IL-6-specific antibody labeled with a ruthenium complex and streptavidin-coated microparticles, the antibodies form with the antigen of the sample a sandwich complex.

The reaction mixture is aspirated into the measuring cell where the microparticles are magnetically captured onto the surface of the electrode. Unbound substances are then removed with ProCell. Application of a voltage to the electrode then induces chemiluminescent emission which is measured by a photomultiplier.

Results are determined via a calibration curve which is instrument-specifically generated by 2-point calibration and a master curve provided via the reagent barcode. All concentration values are calculated from raw signal using the calibration curve. The reference value was set to 100% for the first measurement (day 0). The analyzer automatically calculates the analyte concentration of each sample in pg/mL. All other calculations were done using Excel 2003 from Microsoft.

Example 1

Two concentrations of IL-6 (24.4-42.9 pg/mL and 126.8-234.2 pg/mL) were prepared in a composition based on equine serum.

Of each IL-6 concentration 6 aliquots were prepared. First aliquot was spiked with 0.05% TTAB, second aliquot was spiked with 0.1% TTAB, third aliquot was spiked with 0.15% TTAB, fourth aliquot was spiked with 0.2% TTAB, fifth aliquot was spiked with 0.25% TTAB, sixth aliquot was spiked with 0.5% TTAB.

The concentration of IL-6 was measured using the ELECSYS IL-6 immunoassay from all 12 aliquots, measurement was performed within 30 minutes after addition of the IL-6. This IL-6 measurement served as reference in this experiment. At day 0, when the first measurement was performed, the reference value was set to 100%.

All 12 aliquots were stored up to 5 days at 2-8 C. Samples were taken and measured for IL-6 after 1, 4 and 5 days. After 5 days the recovery of IL-6 was still between 88%-94% using a concentration of 0.15% TTAB-0.25% TTAB, while the recovery is only 72% for a concentration of 0.5% TTAB and 82% for a concentration of 0.05% TTAB using a low concentration of IL-6 (24.4-42.9 pg/ml). Using a high concentration of IL-6 (126.8-234.2 pg/ml) the recovery was between 90-94% for 0.15% TTAB-0.25% TTAB, while the recovery of IL-6 is only 77% for a concentration of 0.5% TTAB and 85% for a concentration of 0.05% TTAB.

Detailed results are shown in FIG. 1. This experiment clearly indicates the concentration dependant stabilization effect of TTAB towards IL-6 as determined by measuring the % recovery. Best stabilization is observed with 0.2% and 0.25% TTAB. By contrast, 0.5% TTAB leads to a decrease in stability.

Example 2

Two concentrations of IL-6 (43.7-60.8 pg/mL and 258.5-347.5 pg/mL) were prepared in a composition based on equine serum.

Of each IL-6 concentration 3 aliquots were prepared. First aliquot was used as negative control and stayed unchanged, second aliquot was spiked with 0.2% TTAB, third aliquot was spiked with 0.25% TTAB.

The concentration of IL-6 was measured using the ELECSYS IL-6 immunoassay from all 6 aliquots, measurement was performed within 30 minutes after addition of the IL-6. This IL-6 measurement served as reference for samples stored 23 days at 2-8° C. in this experiment.

All 6 aliquots were stored up to 23 days at 2-8° C. Samples were taken and measured for IL-6 after 1, 3, 4 and 23 days. The recovery of the reference values was set to 100% when the first samples of all 6 aliquots were taken (day 0).

After 23 days of storage of the samples the recovery values are still between 93% for 0.2% TTAB and 94% for 0.25% TTAB in low concentration of IL-6 (43.7-60.8 pg/mL). When using no TTAB in the aliquots the recovery value decreases to 74% after 23 days of storage of the samples.

Using a high concentration of IL-6 (258.5-347.5 pg/mL) the recovery values are still between 95% for 0.2% TTAB and 96% for 0.25% TTAB. When using no TTAB in the aliquots the recovery value decreases to 78% after 23 days of storage of the samples.

Detailed results are shown in FIG. 2. This experiment clearly confirms the stabilization effect observed with 0.2% and 0.25% TTAB on the % recovery of IL-6. The negative control without TTAB shows a reduced stability.

Example 3a

Two concentrations of IL-6 (29.1-44.1 pg/mL and 169.1-241.8 pg/mL) were prepared in a composition based on human serum.

Of each IL-6 concentration 4 aliquots were prepared. First aliquot was used as negative control and stayed unchanged, second aliquot was spiked with 0.2% TTAB, third aliquot was spiked with 0.2% DTAB, fourth aliquot was spiked with 0.2% HTAB.

The concentration of IL-6 was measured using the ELECSYS IL-6 immunoassay from all 8 aliquots, measurement was performed within 30 minutes after addition of the IL-6. This IL-6 measurement served as reference in this experiment.

All 8 aliquots were stored up to 30 days at 2-8° C. Samples were taken and measured for IL-6 after 1, 2, 3, 7, 16 and 30 days.

The recovery of the reference values for the aliquots was set 100% (day 0) when the first measurements were performed. A positive effect of the addition of a compound of the formula $C_{10}$-$C_{18}$-alkyl trimethylammonium halogenide (I) is still existing after 30 days of storage of the aliquots. While the negative control shows a recovery value of 28% for a low concentration of IL-6, the recovery values for aliquots with 0.2% TTAB, 0.2% DTAB or 0.2% HTAB is still between 40-52%. The same effect is visible for a high concentration of IL-6, the negative control shows a recovery value of 27% for a low concentration of IL-6, the recovery values for aliquots with 0.2% TTAB, 0.2% DTAB or 0.2% HTAB is between 39-48%.

Detailed results are shown in FIG. 3a. This experiment clearly indicates the stabilization effect observed with 0.2% TTAB or 0.2% DTAB or 0.2% HTAB in a composition based on human serum. The negative control without compound shows a reduced stability.

Example 3b

Two concentrations of IL-6 (33.6-44.1 pg/mL and 187.2-268.3 pg/mL) were prepared in a composition based on equine serum.

Of each IL-6 concentration 4 aliquots were prepared. First aliquot was used as negative control and stayed unchanged, second aliquot was spiked with 0.2% TTAB, third aliquot was spiked with 0.2% DTAB, fourth aliquot was spiked with 0.2% HTAB.

IL-6 was measured using the ELECSYS IL-6 immunoassay from all 8 aliquots, measurement was performed within 30 minutes after addition of the IL-6. The IL-6 measurement served as reference in this experiment.

All 8 aliquots were stored up to 30 days at 2-8° C. Samples were taken and measured for IL-6 after 1, 2, 3, 7, 16 and 30 days.

The recovery of the reference values for the aliquots was set 100% (day 0) when the first measurements were performed. A positive effect of the addition of a compound of the formula $C_{10}$-$C_{18}$-alkyl trimethylammonium halogenide (I) is still existing after 30 days of storage of the aliquots. While the negative control shows a recovery value of 79% for a low concentration of IL-6, the recovery values for aliquots with 0.2% TTAB, 0.2% DTAB or 0.2% HTAB is still between 93-95%. The same effect is visible for a high concentration of IL-6, the negative control shows a recovery value of 80% for a low concentration of IL-6, the recovery values for aliquots with 0.2% TTAB, 0.2% DTAB or 0.2% HTAB is between 89-93%.

Detailed results are shown in FIG. 3b. This experiment clearly indicates the stabilization effect observed with 0.2% TTAB or 0.2% DTAB or 0.2% HTAB in a composition based on equine serum. The negative control without compound shows a reduced stability.

Example 4

Two concentrations of IL-6 (41.4-53.1 pg/mL and 237.7-285.0 pg/mL) were prepared in an aqueous based solution containing 3% serum protein, commercially available from Roche (Universal Diluent, Cat. No. 03183971122)

Of each IL-6 concentration 4 aliquots were prepared. First aliquot was used as negative control and stayed unchanged, second aliquot was spiked with 0.2% TTAB, third aliquot was spiked with 0.2% DTAB, fourth aliquot was spiked with 0.2% HTAB.

The concentration of IL-6 was measured using the ELECSYS IL-6 immunoassay from all 8 aliquots, measurement was performed within 30 minutes after addition of the IL-6. This IL-6 measurement served as reference in this experiment.

All 8 aliquots were stored up to 30 days at 2-8° C. Samples were taken and measured for IL-6 after 7, 16 and 30 days.

The recovery of the reference values for the aliquots was set 100% (day 0) when the first measurements were performed. A negative effect of the addition of a compound of the formula $C_{10}$-$C_{18}$-alkyl trimethylammonium halogenide (I) is already observed after 7 days of storage of the aliquots. While the negative control shows a recovery value of 98% for a low concentration of IL-6, the recovery values for aliquots with 0.2% TTAB, 0.2% DTAB or 0.2% HTAB is only between 60-81%. The same effect is visible for a high concentration of IL-6, the negative control shows a recovery value of 96%, the recovery values for aliquots with 0.2% TTAB, 0.2% DTAB or 0.2% HTAB is only between 59-81%.

Detailed results are shown in FIG. 4. This experiment clearly indicated the negative effect of TTAB, or DTAB or HTAB on the stability of IL-6 in an aqueous based solution.

Example 5

IL-6 was added to a solution based on equine, bovine or mouse serum (203.1-254.2 pg/mL) and four HEPES buffer.

Of each IL-6 preparation 2 aliquots were prepared. First aliquot was used as negative control and stayed unchanged, second aliquot was spiked with 0.225% TTAB.

IL-6 was measured using the ELECSYS IL-6 immunoassay from all 6 aliquots, measurement was performed within 30 minutes after addition of the IL-6. This IL-6 measurement served as reference in this experiment.

All 6 aliquots were stored 7 days at 2-8° C. Samples were taken and measured for IL-6 after 7 days.

Detailed results are shown in FIG. 5. This experiment clearly indicated the positive effect of TTAB on the stability of IL-6 in a composition, based on equine, bovine and mouse serum. It also indicates the negative effect of TTAB on the stability of IL-6 in bovine serum.

What is claimed is:

1. A liquid composition comprising
   interleukin 6 (IL-6) or an isoform or fragment thereof,
   a compound of the formula $C_{10}$-$C_{18}$-alkyl trimethylammonium halogenide, wherein the compound is saturated or unsaturated and/or substituted or unsubstituted, or a salt thereof, and wherein the concentration of the compound in the composition is about 0.15% to about 0.4%, and
   a serum.

2. The composition of claim 1 wherein the compound stabilizes IL-6.

3. The composition of claim 1 wherein the compound is of the formula $C_{12}$-$C_{16}$-alkyl trimethylammonium halogenide.

4. The composition of claim 1 wherein the halogenide is selected from the group consisting of fluoride, chloride, bromide, and iodide.

5. The composition of claim 1 wherein the compound is unsaturated.

6. The composition of claim 1 wherein the compound is unsubstituted.

7. The composition of claim 1 wherein the compound is selected from the group consisting of tetradecyl trimethylammonium bromide, dodecyl trimethylammonium bromide, and hexadecyl trimethylammonium bromide.

8. The composition of claim 1 wherein the concentration of the compound in the composition is about 0.15% to about 0.25%.

9. The composition of claim 1 wherein the serum is mammalian serum selected from the group consisting of human, equine, bovine, sheep, and mouse serum.

10. A method of producing a composition according to claim 1 comprising the steps of
    forming a mixture of interleukin 6 (IL-6) or an isoform or fragment thereof,
    a compound of the formula $C_{10}$-$C_{18}$-alkyl trimethylammonium halogenide, wherein the compound is saturated or unsaturated and/or substituted or unsubstituted, or a salt thereof, wherein the concentration of the compound in the composition is about 0.15% to about 0.4%, and
    a serum, and
    optionally lyophilizing the mixture.

11. A lyophilized composition comprising interleukin 6 (IL-6) or an isoform or fragment thereof, a compound of the formula $C_{10}$-$C_{18}$-alkyl trimethylammonium halogenide, wherein the compound is saturated or unsaturated and/or substituted or unsubstituted, or a salt thereof, and wherein the concentration of the compound in the composition is about 0.15% to about 0.4%, and a serum.

12. A kit comprising instructions for use and a composition or a lyophilisate comprising:
    interleukin 6 (IL-6) or an isoform or fragment thereof,
    a compound of the formula $C_{10}$-$C_{18}$-alkyl trimethylammonium halogenide, wherein the compound is saturated or unsaturated and/or substituted or unsubstituted, or a salt thereof, and wherein the concentration of the compound in the composition is about 0.15% to about 0.4%, and a serum.

13. A method of stabilizing interleukin 6 (IL-6) or an isoform or fragment thereof comprising the steps of forming a mixture of interleukin 6 (IL-6) or an isoform or fragment thereof, a compound of the formula $C_{10}$-$C_{18}$-alkyl trimethylammonium halogenide, wherein the compound is saturated or unsaturated and/or substituted or unsubstituted, or a salt thereof, wherein the concentration of the compound in the composition is about 0.15% to about 0.4%, and a serum, whereby the compound stabilizes the IL-6.

* * * * *